United States Patent
Gaudoin et al.

(10) Patent No.: US 6,652,485 B1
(45) Date of Patent: Nov. 25, 2003

(54) BALLOON SHOULDER DESIGNS

(75) Inventors: Henri A. Gaudoin, Mountain View, CA (US); David T. Jacobson, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/585,885

(22) Filed: May 31, 2000

(51) Int. Cl.$^7$ ............................................. A61M 31/00
(52) U.S. Cl. ................................. 604/103.07; 604/916
(58) Field of Search .................. 604/96.01, 103.06, 604/103.07, 103.08, 103.11, 103.14, 915, 916, 921; 606/192, 194, 108

(56) References Cited

U.S. PATENT DOCUMENTS

| | | | |
|---|---|---|---|
| 4,456,000 A | 6/1984 | Schjeldahl et al. ............ 128/1 |
| 4,941,877 A | 7/1990 | Montano, Jr. ................. 604/96 |
| 5,015,230 A | 5/1991 | Martin et al. ................. 604/96 |
| 5,037,392 A | 8/1991 | Hillstead ..................... 604/96 |
| 5,041,125 A | 8/1991 | Montano, Jr. ............... 606/192 |
| 5,076,268 A | * 12/1991 | Weber ................... 128/207.14 |
| 5,163,989 A | 11/1992 | Campbell et al. ............. 65/110 |
| 5,195,970 A | 3/1993 | Gahara ........................ 604/96 |
| 5,226,887 A | 7/1993 | Farr et al. ..................... 604/96 |
| 5,250,070 A | 10/1993 | Parodi ......................... 606/94 |
| 5,304,132 A | * 4/1994 | Jang ....................... 604/101.01 |
| 5,334,146 A | 8/1994 | Ozasa .......................... 604/96 |
| 5,456,666 A | 10/1995 | Campbell et al. ............. 604/96 |
| 5,478,319 A | 12/1995 | Campbell et al. ............. 604/96 |
| 5,545,132 A | 8/1996 | Fagan et al. .................. 604/96 |
| 5,645,529 A | 7/1997 | Fagan et al. ................. 604/101 |
| 5,718,680 A | * 2/1998 | Kraus et al. ................. 128/898 |
| 5,769,817 A | 6/1998 | Burgmeier ................... 604/96 |
| 5,826,588 A | 10/1998 | Forman ...................... 128/898 |
| 5,853,389 A | 12/1998 | Hijlkema ..................... 604/96 |

* cited by examiner

*Primary Examiner*—LoAn H. Thanh
(74) *Attorney, Agent, or Firm*—Fulwider Patton Lee & Utecht, LLP

(57) ABSTRACT

An inflatable member suitable for angioplasty or other medical procedures comprising asymmetric conic shoulder portions that optimize the wrapped profile. The asymmetry distributes the inflatable member material of the shoulder portions over a larger area to reduce the inflatable member profile and improve flexibility. Optionally, the asymmetrical shoulder portions preformed creases to facilitate folding. In an alternate embodiment, each shoulder portion has at least three radially spaced preformed creases to optimize folding in the shoulder portion. The invention also comprises methods of forming such inflatable members, the methods generally comprising using molds having the requisite characteristics. Specifically, the mold may have ridges within the areas corresponding the shoulder portions to form the preformed creases when the inflatable member is blow molded.

9 Claims, 2 Drawing Sheets

BALLOON SHOULDER DESIGNS

FIELD OF INVENTION

The invention relates to the field of intravascular delivery systems, and more particularly to dilatation balloon catheters.

BACKGROUND OF THE INVENTION

Angioplasty balloons must be able to expand to a relatively large diameter in order to dilate stenosed regions of the vasculature effectively. However, it is also desirable for the angioplasty balloons to exhibit a minimal profile when deflated to facilitate introduction into and travel within the vasculature. A small crossing profile also allows the balloon to be positioned across the lesion. Furthermore, the deflated balloon should be sufficiently flexible to allow the balloon to be advanced through the often tortuous coronary anatomy.

To obtain a minimized deflated profile, the prior art has adopted various strategies to cause the balloon to preferentially fold into a compact shape when deflated. Typically, these strategies involve preformed creases that cause the balloon material to fold into flaps that then may be wrapped to minimize profile. Nevertheless, these attempts remain an incomplete solution to the problems of minimizing balloon profile.

One significant problem flows from the techniques used to manufacture the balloons. Typically, a parison is blow molded into the expanded balloon shape that generally comprises a main cylindrical section having a working diameter with flanking shoulder regions that provide a transition from the expanded working diameter of the balloon to the nominal diameter of the catheter. To provide sufficient material for blow molding in the areas corresponding to the working length, the parison must be relatively thick-walled. Upon expansion during blow molding, the material in the main cylindrical section is efficiently used leaving it relatively thin walled. However, the resulting wall thickness in the shoulder areas varies depending upon the final diameter. Since the areas at the extremities of the balloon essentially do not expand, the balloon material remains relatively thick in these areas. This varying wall thickness in the shoulder areas leads to inefficient folding and does not allow for an optimum deflated profile.

Another difficulty related to balloon folding results when the preformed creases converge in the shoulder regions. Where more than one crease occurs in a given area, the flaps of balloon material tend to stack, leading to increased profile and decreased flexibility.

Accordingly, there remains a need to provide angioplasty balloon designs that allow deflation to a small diameter while remaining flexible. Specifically, there remains a need for designs that minimize the difficulties resulting from the varying amount of balloon material in the shoulder regions. There is a corresponding need for methods of conveniently manufacturing such designs. This invention satisfies these and other needs.

SUMMARY OF THE INVENTION

The invention is an inflatable member comprising a generally cylindrical working length having an inflated diameter and opposing ends with tapered shoulder portions, wherein the shoulder portions are configured to minimize the deflated profile of the inflatable member. In a preferred embodiment, the shoulder portions have an asymmetric conic configuration. The asymmetry distributes the inflatable member material of the shoulder portions over a larger area than possible with a symmetrical configuration that reduces the inflatable member profile and improves flexibility. Optionally, the asymmetrical shoulder portions may also have spiraling preformed creases to facilitate folding. In an alternate embodiment, each shoulder portion has at least one triangular shaped pattern of preformed creases to optimize folding in the shoulder portion. Optionally, the shoulder portions may also have an asymmetric configuration and may have more than three preformed creases.

The inflatable members of the invention may generally be made by blow molding a conventional thermoplastic parison. Preferably, the mold is configured to produce inflatable members having the asymmetrical shoulder portions. The mold may also have ridges formed in the shoulder portion to provide the preformed crease in the blown inflatable member. Generally, the parison is placed within the mold, the mold is heated, and inflation fluid is supplied to the interior of the parison at sufficient pressure to expand it and conform it to the mold.

DETAILED DESCRIPTION OF THE INVENTION

Figure 1:
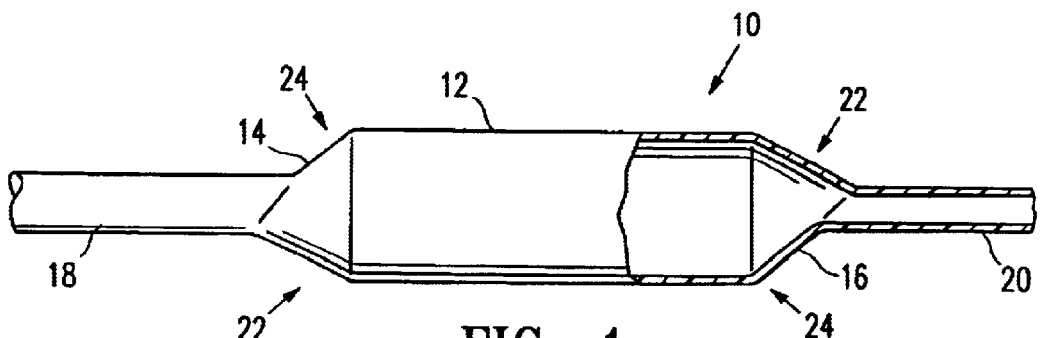
FIGS. 1 and 2 are elevational, partially cut away, views of alternate embodiments of an inflatable member having the asymmetrical shoulder portions characteristic of the invention.

FIG. 1 illustrates features of an inflatable member 10 having characteristics of the invention that generally comprise a cylindrical working length 12 and tapered shoulder portions 14 and 16. The shoulder portions provide the transition in diameter from the working diameter of the inflatable member to the nominal diameter of the catheter. For example, the inflatable member 10 shown in FIG. 1 is configured for use with an over-the-wire type catheter which generally comprises an inner tubular member coaxially disposed within the catheter shaft. Thus, shoulder portion 14 provides a transition from the working diameter to a diameter at proximal portion 18 that corresponds to the catheter shaft while shoulder portion 16 transitions to a smaller diameter at distal portion 20 to correspond to the inner tubular member. In this embodiment, the shoulder portions 14 and 16 have an asymmetrical conical configuration that allow for a minimized deflated profile while maintaining good flexibility. In FIG. 1, the asymmetry is manifested by the circumferentially varying angle between the surface of the working length 12 and the shoulder portion 14 or 16. For example, the angle is the greatest at position 22 and the least at position 24, where positions 22 and 24 are radially opposed.

Figure 2:
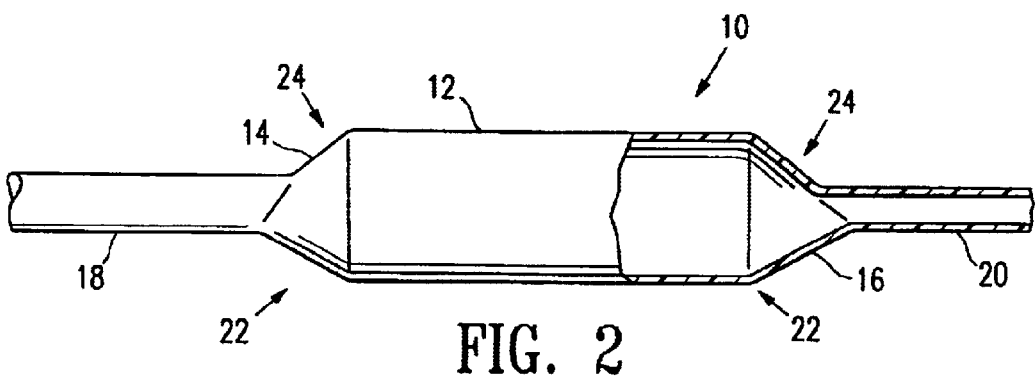

An alternative example is shown in FIG. 2, in which the asymmetry is manifested as skewing along the longitudinal axis. In the embodiment shown in FIG. 1, the corresponding asymmetries of each shoulder portion are rotated 180° with respect to each other while in FIG. 2 they are axially aligned. However, the corresponding asymmetries may be placed in any relation to each other. Further, each shoulder portion may have its own particular asymmetrical configuration.

Figure 3:
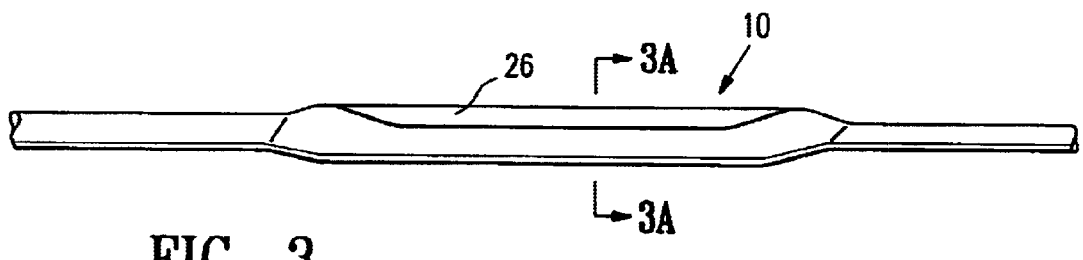
FIG. 3 is an elevational view of a wrapped inflatable member having asymmetrical shoulder portions.
Figure 3A:
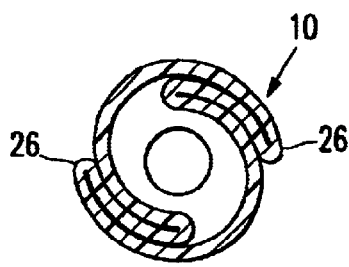
FIG. 3A is a transverse cross sectional view of the inflatable member of FIG. 3 taken along line 3A—3A.

FIG. 3 illustrates the advantages obtained by using the asymmetrical shoulder portions 14 and 16. Specifically, when inflatable member 10 is in a deflated condition, the excess inflatable member material forms flaps 26 that may be wrapped around the catheter shaft to minimize the profile of the system. The asymmetrical shoulder portions tend to offset the flaps 26 from each other, distributing the wrapped inflatable member material over a greater length of the catheter shaft. This is especially important in the shoulder region where, as described above, the inflatable member material has a greater wall thickness since it has not been expanded to the same degree as the material in the working length. In addition a decrease in the profile diameter, this configuration also improves the flexibility of the wrapped inflatable member to facilitate placement within the vasculature. FIG. 3A illustrates transverse cross sectional view of the inflatable member shown in FIG. 3, taken along line 3A—3A.

FIG. 3 illustrates the advantages obtained by using the asymmetrical shoulder portions 14 and 16. Specifically, when inflatable member 10 is in a deflated condition, the excess inflatable member material forms flaps 26 that may be wrapped around the catheter shaft to minimize the profile of the system. The asymmetrical shoulder portions tend to offset the flaps 26 from each other, distributing the wrapped inflatable member material over a greater length of the catheter shaft. This is especially important in the shoulder region where, as described above, the inflatable member material has a greater wall thickness since it has not been expanded to the same degree as the material in the working length. In addition a decrease in the profile diameter, this configuration also improves the flexibility of the wrapped inflatable member to facilitate placement within the vasculature. FIG. 3A illustrates transverse cross sectional view of the inflatable member shown in FIG. 3, taken along line 3—3.

Figure 4:
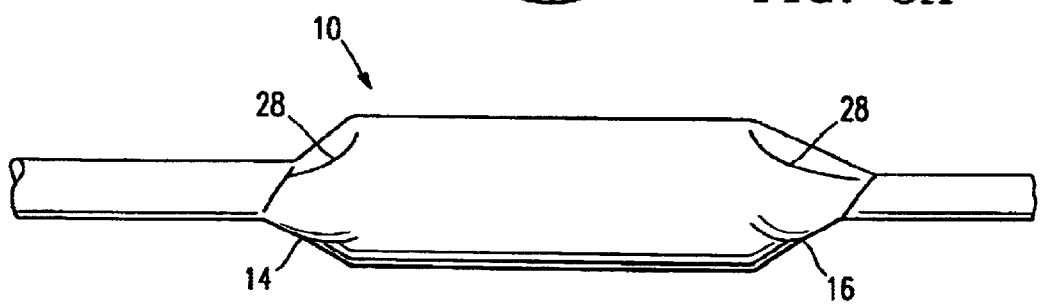
FIG. 4 shows a further embodiment of the invention shown in FIG. 1, having the asymmetrical shoulder portions together with spiral preformed creases.

The embodiment in FIG. 4 shows the asymmetrical shoulder portions 14 and 16 together with spiral preshaped creases 28 in the shoulder portions. The spiral creases 28 enhance the folding of inflatable member 10. Preferably, two or more spiral creases 28 should be provided for each shoulder portion. Further, the preformed creases may have other suitable configurations to minimize the wrapped profile.

Figure 5:
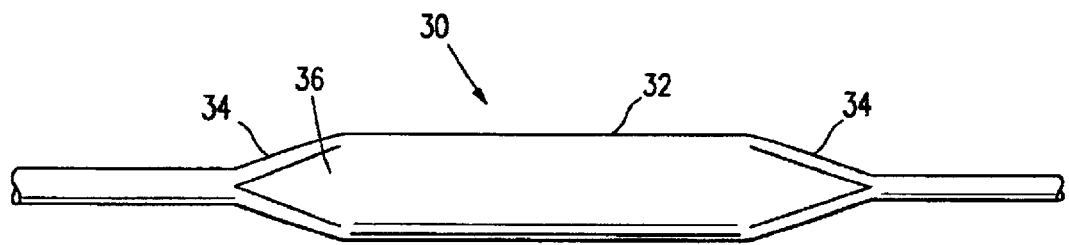
FIG. 5 is an elevational view of an alternate embodiment of the invention showing an inflatable member having triangular preformed creases in the shoulder portions.
Figure 6:
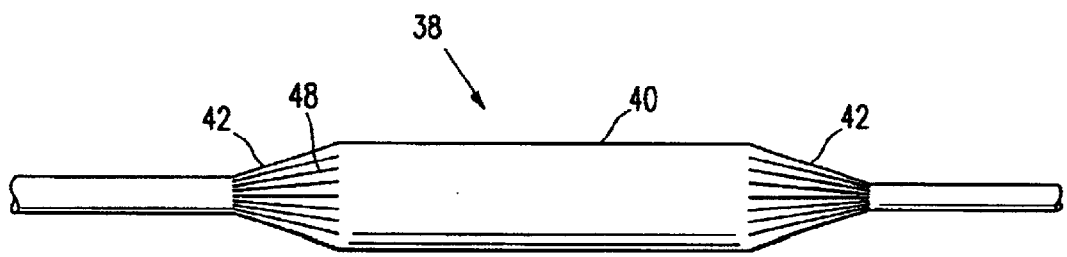
FIG. 6 is an elevational view of yet another embodiment of the invention showing an inflatable member having multiple preformed creases in the shoulder portions.

FIGS. 5 and 6 show an alternate embodiment of the invention. In FIG. 5, inflatable member 30 has a cylindrical working portion 32 and tapered shoulder portions 34 at either end. The shoulder portions 34 have three, radially spaced preformed creases 36 in a triangular pattern to enhance folding in the shoulder region. In an alternative embodiment, shown in FIG. 6, inflatable member 38 has a cylindrical working portion 40 and tapered shoulder portions 42 that have four or more preformed creases 48. Again, creases 48 facilitate folding of the inflatable member and minimize the bulkiness of the material in the shoulder region.

Figure 7:
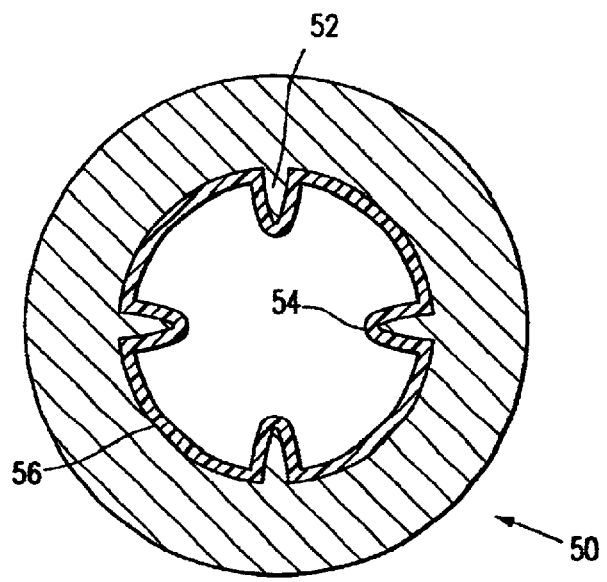
FIG. 7 is an cross sectional view of a mold useful in the practice of the invention.

The invention also comprises methods of manufacturing inflatable members. Generally, the methods employ a mold 50 having tapered regions for forming the inflatable member shoulder portions. As shown in cross section in FIG. 7, mold 50 has ridges 52 formed along the interior surface to create creases 54 in the shoulder portion of an inflatable member 56. Preferably, conventional blow molding techniques may be used. For example, a parison is placed within the mold 50 and inflation fluid is introduced into the interior of the parison to stretch and expand the material into the final inflatable member shape. As conventionally practiced, it may be desirable to axially orient the polymer molecules by prestretching the parison.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. An inflatable member configured for use with an elongated tubular member having an outer diameter and a longitudinal axis, comprising a generally cylindrical working length having a working diameter and asymmetric conical shoulder portions at opposing ends of the working length that taper from the working diameter to the outer diameter of the elongate tubular member, wherein the asymmetric conical shoulder portions intersect the elongate tubular member so as to define a plane that is not perpendicular to the longitudinal axis of the elongate tubular member.

2. The inflatable member of claim 1 wherein the asymmetric conic shoulder portions have performed creases.

3. The inflatable member of claim 2, wherein the preformed creases have a spiral configuration.

4. The inflatable member of claim 1 wherein the asymmetric conical shoulder portions define an angle between the working diameter of the inflatable member and the outer diameter of the elongated tubular member that varies in the circumferential direction.

5. The inflatable member of claim 1 wherein the asymmetric conical shoulder portions intersect the elongated tubular member to define an ellipse.

6. The inflatable member of claim 1 wherein the asymmetric conical shoulder portions are configured to allow a minimized wrapped profile.

7. The inflatable member of claim 1 wherein the asymmetric conical shoulder portions have corresponding asymmetric features that are axially aligned.

8. The inflatable member of claim 1 wherein the asymmetric conical shoulder portions have corresponding asymmetric features that are axially rotated.

9. The inflatable member of claim 1 wherein the asymmetric conical shoulder portions are configured to create longitudinally offset flaps when the inflatable member is wrapped around the elongated tubular member.

\* \* \* \* \*

UNITED STATES PATENT AND TRADEMARK OFFICE
CERTIFICATE OF CORRECTION

PATENT NO. : 6,652,485 B1
DATED : November 25, 2003
INVENTOR(S) : Henri A. Gaudoin and David T. Jacobson It is certified that error appears in the above-identified patent and that said Letters Patent is hereby corrected as shown below:

Column 3,
Lines 30 through 47, delete the entire paragraph.

Signed and Sealed this

First Day of June, 2004

JON W. DUDAS
*Acting Director of the United States Patent and Trademark Office*